United States Patent [19]

Bedekovic et al.

[11] Patent Number: 4,675,407

[45] Date of Patent: Jun. 23, 1987

[54] RING-SUBSTITUTED 4-AZAPHTHALIDES

[75] Inventors: Davor Bedekovic, Cheshire, England; Ian J. Fletcher, Magden, Switzerland

[73] Assignee: Ciba-Geigy Corporation, Ardsley, N.Y.

[21] Appl. No.: 816,464

[22] Filed: Jan. 6, 1986

[30] Foreign Application Priority Data

Jan. 15, 1985 [CH] Switzerland ............... 163/85

[51] Int. Cl.⁴ .................................. C07D 471/048
[52] U.S. Cl. .................................. 546/116; 503/220
[58] Field of Search .................................. 546/116

[56] References Cited

U.S. PATENT DOCUMENTS

| | | | |
|---|---|---|---|
| 3,775,424 | 11/1973 | Farber | 546/116 |
| 3,916,070 | 10/1975 | Ozutsumi et al. | 546/116 X |
| 3,936,564 | 2/1976 | Miyazawa et al. | 428/307 |
| 4,046,776 | 9/1977 | Garner et al. | 546/116 X |
| 4,102,893 | 7/1978 | Garner et al. | 548/456 |
| 4,275,905 | 6/1979 | Miller | 282/27.5 |
| 4,299,411 | 6/1979 | Brockett | 282/27.5 |
| 4,334,072 | 6/1982 | Becker et al. | 546/112 |
| 4,508,897 | 4/1985 | Bedekovic et al. | 546/116 X |
| 4,564,679 | 1/1986 | Fujino et al. | 546/116 |

FOREIGN PATENT DOCUMENTS

| | | |
|---|---|---|
| 2445333 | 9/1978 | France . |
| 49-118515 | 11/1974 | Japan . |
| 50-3426 | 1/1975 | Japan . |
| 1443617 | 7/1976 | United Kingdom . |
| 2006248 | 5/1979 | United Kingdom . |
| 2031934 | 4/1980 | United Kingdom . |
| 2075042 | 11/1981 | United Kingdom . |
| 2103234 | 2/1983 | United Kingdom . |

Primary Examiner—Richard L. Raymond
Attorney, Agent, or Firm—Edward McC. Roberts; Meredith C. Findlay

[57] ABSTRACT

The invention relates to ring-substituted 4-azaphthalides of formula

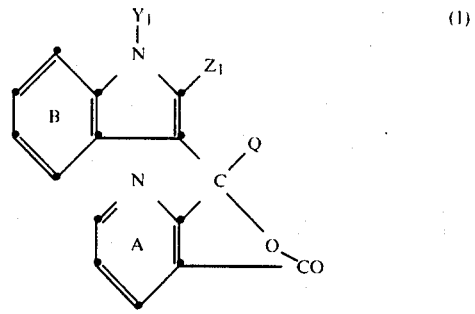

wherein
Q is a substituted phenyl radical of the formula

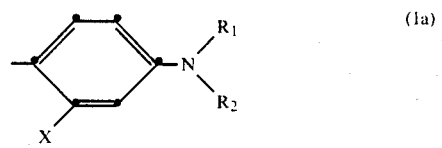

or a 3-indolyl radical of the formula

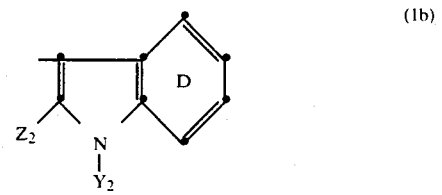

$Y_1$ and $Y_2$ are hydrogen, unsubstituted or substituted alkyl, acyl, or unsubstituted or substituted benzyl,
$Z_1$ and $Z_2$ are hydrogen, lower alkyl or phenyl,
$R_1$ and $R_2$, together with the nitrogen atom to which they are attached, are a 5- or 6-membered, preferably saturated, heterocyclic ring,
X is hydrogen, halogen, alkyl, alkoxy, acyloxy, benzyl, phenyl, benzyloxy, phenoxy, substituted benzyl or benzyloxy, or is the —$NT_1T_2$ group, in which $T_1$ and $T_2$ are hydrogen, lower alkyl, cycloalkyl, unsubstituted or substituted benzyl or is acyl, and $T_1$ is also unsubstituted or substituted phenyl, and wherein the pyridine ring A is substituted by lower alkyl, lower alkoxy, lower alkylthio, phenyl, phenoxy, or phenyl or phenoxy each substituted by halogen, cyano, lower alkyl, lower alkoxy or cyano-lower alkyl, or by tetramethylene, and the benzene nuclei B and D are unsubstituted or substituted.

These compounds are particularly suitable for use as color formers in pressure-sensitive or heat-sensitive recording materials. They are pH-stable and, depending on the meaning of Q, give strong blue or reddish-violet colorations of excellent lightfastness.

16 Claims, No Drawings

RING-SUBSTITUTED 4-AZAPHTHALIDES

The present invention relates to 4-azaphthalides which are substituted in the pyridine ring, to their preparation and to the use thereof as colour formers in pressure-sensitive or heat-sensitive recording materials.

The ring-substituted azaphthalides of this invention are characterised by the formula

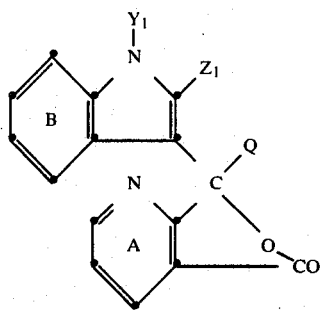

(1)

wherein
Q is a substituted phenyl radical of the formula

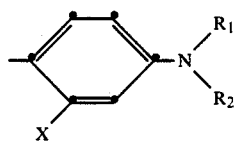

(1a)

or a 3-indolyl radical of the formula

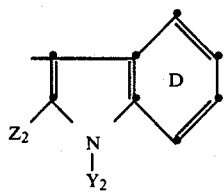

(1b)

$Y_1$ and $Y_2$ are each independently of the other hydrogen, alkyl of not more than 12 carbon atoms which is unsubstituted or substituted by halogen, hydroxyl, cyano or lower alkoxy, or are $C_1-C_{12}$acyl, benzyl, or benzyl which is substituted by halogen, cyano, lower alkyl or lower alkoxy, $Z_1$ and $Z_2$ are each independently of the other hydrogen, lower alkyl or phenyl, $R_1$ and $R_2$ are each independently of the other hydrogen, alkyl of not more than 12 carbon atoms which is unsubstituted or substituted by halogen, hydroxy, cyano or lower alkoxy, or are $C_5-C_{10}$cycloalkyl, or benzyl or phenyl, each unsubstituted or substituted by halogen, cyano, lower alkyl or lower alkoxy; or $R_1$ and $R_2$, together with the nitrogen atom to which they are attached, are a 5- or 6-membered, preferably saturated, heterocyclic ring, X is hydrogen, halogen, lower alkyl, $C_1-C_{12}$alkoxy, $C_1-C_{12}$acyloxy, benzyl, phenyl, benzyloxy, phenoxy, or benzyl or benzyloxy which are each substituted by halogen, cyano, lower alkyl or lower alkoxy, or is the $-NT_1T_2$ group, in which $T_1$ and $T_2$, each independently of the other, are hydrogen, lower alkyl, cycloalkyl, benzyl, or benzyl which is substituted by halogen, cyano, lower alkyl or lower alkoxy, or is $C_1-C_{12}$acyl, and $T_1$ is also phenyl, or phenyl which is substituted by halogen, cyano, lower alkyl or lower alkoxy, and wherein the pyridine ring A is substituted by lower alkyl, lower alkoxy, lower alkylthio, phenyl, phenoxy, or phenyl or phenoxy which are each substituted by halogen, cyano, lower alkyl, lower alkoxy or cyano-lower alkyl, or by tetramethylene, and the benzene nuclei B and D, each independently of the other, are unsubstituted or substituted by halogen, cyano, lower alkyl, lower alkoxy, lower alkoxycarbonyl, amino, mono-lower alkylamino or di-lower alkylamino.

Within the scope of the definition of the azaphthalides, lower alkyl, lower alkylthio and lower alkoxy denote those groups are moieties which contain 1 to 5, preferably 1 to 3, carbon atoms. Examples of lower alkyl groups are: ethyl, n-propyl, isopropyl, n-butyl, sec-butyl, amyl or isoamyl. Lower alkoxy groups are for example: methoxy, ethoxy, isopropoxy, isobutoxy or tert-butoxy. Lower alkylthio groups are for example: methylthio, ethylthio, propylthio or butylthio.

Acyl is in particular formyl, lower alkylcarbonyl, e.g. acetyl or propionyl, or benzoyl. Further acyl radicals may be lower alkylsulfonyl, e.g. methylsulfonyl or ethylsulfonyl as well as phenylsulfonyl.

Benzoyl and phenylsulfonyl may be substituted by halogen, methyl, methoxy or ethoxy. An acyloxy radical X may be formyloxy, lower alkylcarbonyloxy or benzoyloxy. X as $C_1-C_{12}$alkoxy may be a straight chain or branched group such as methoxy, ethoxy, isopropoxy, tert-butoxy, n-hexyloxy, octyloxy or dodecyloxy.

$R_1$, $R_2$, $Y_1$ and $Y_2$ as alkyl groups may be straight chain or branched alkyl groups, e.g. methyl, ethyl, n-propyl, isopropyl, n-butyl, sec-butyl, tert-butyl, amyl, isoamyl, n-hexyl, 2-ethyl-n-hexyl, n-heptyl, n-octyl, isooctyl, n-nonyl, isononyl or n-dodecyl.

Substituted alkyl groups $R_1$, $R_2$, $Y_1$ and $Y_2$ are preferably cyanoalkyl, haloalkyl, hydroxyalkyl, alkoxyalkyl, each containing preferably a total of 2 to 4 carbon atoms. Such groups are e.g. β-cyanoethyl, β-chloroethyl, β-hydroxyethyl, β-methoxyethyl or β-ethoxyethyl.

Cycloalkyl groups $R_1$, $R_2$, $T_1$ and $T_2$ are cyclopentyl, cycloheptyl or, preferably, cyclohexyl. The cycloalkyl groups may contain one or more $C_1-C_4$alkyl groups, preferably methyl groups, and contain a total of 5 to 10 carbon atoms.

Preferred substituents of the benzyl moiety of radicals R, T, X and Y, of the phenyl moiety of $R_1$, $R_2$ and $T_1$, and of the benzyloxy group X, are e.g. halogen, methyl or methoxy. Examples of such araliphatic and aromatic radicals are p-methylbenzyl, o or p-chlorobenzyl, o- or -p-tolyl, xylyl, o-, m- or p-chlorophenyl, o- or p-methoxyphenyl, o- or p-chlorobenzyloxy or o- or p-methylbenzyloxy.

A heterocyclic ring $-NR_1R_2$ is for example a pyrrolidino, piperidino, pipecolino, morpholino, thiomorpholino or piperazino ring, e.g. an N-methylpiperazino ring. Preferred saturated heterocyclic rings $-NR_1R_2$ are pyrrolidino, piperidino or morpholino.

The substituents $R_1$ and $R_2$ are preferably cyclohexyl, benzyl, cyano-lower alkyl, e.g. β-cyanoethyl or, most preferably, lower alkyl, e.g. methyl or, in particular, ethyl. $-NR_1R_2$ is also preferably pyrrolidinyl.

X may with advantage be hydrogen, halogen, lower alkyl, e.g. methyl, or benzyloxy, $C_1-C_8$alkoxy, preferably lower alkoxy such as methoxy, ethoxy, isopropoxy or tert-butoxy, or the —NT₁T₂ groups, where one of $T_1$ and $T_2$ is preferably $C_1$–$C_8$acyl or lower alkyl and the other is hydrogen or lower alkyl. The acyl radical is in this case preferably lower alkylcarbonyl, e.g. acetyl or propionyl. Preferably X is acetylamino, dimethylamino, benzyloxy or, most preferably, lower alkoxy and, in particular, ethoxy.

The N-substituents $Y_1$ and $Y_2$ are preferably benzyl, acetyl, propionyl or, most preferably, $C_1$–$C_8$alkyl such as methyl, ethyl, n-butyl or, in particular, n-octyl.

$Z_1$ and $Z_2$ are preferably phenyl or, most preferably, methyl.

Examples of alkyl, alkylthio and alkoxy substituents of the pyridine ring A are: methyl, ethyl, n-propyl, isopropyl, n-butyl, isobutyl, tert-butyl, n-pentyl, isoamyl, tert-amyl, methoxy, ethoxy, n-propoxy, isopropoxy, n-butoxy, isobutoxy, tert-butoxy, methylthio, ethylthio, propylthio or butylthio.

Examples of substituted phenyl or phenoxy substituents of the pyridine A are: methylphenyl, ethylphenyl, methoxyphenyl, ethoxyphenyl, chlorophenyl, bromophenyl, fluorophenyl, chlorophenoxy, methylphenoxy, methoxyphenoxy, trifluoromethylphenyl, 2-cyanoethylphenyl, or trifluoromethylphenoxy. If the pyridine ring A carries a tetramethylene group, this group is preferably a tetrahydroquinoline group.

The pyridine ring is preferably substituted by $C_1$–$C_4$alkyl such as methyl, ethyl, propyl, isopropyl, n-butyl, isobutyl or tert-butyl. The pyridine ring A may be mono-, di- or trisubstituted, but is preferably monosubstituted.

The benzene rings B and D are preferably not further substituted. If B and D do carry substituents, then these are preferably halogen or lower alkyl, e.g. methyl.

Interesting ring-substituted 4-azaphthalides are those of the formula

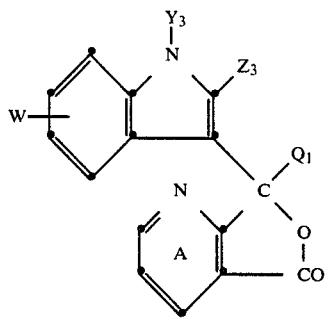

wherein

A has the given meanings and $Q_1$ is a substituted phenyl radical of the formula

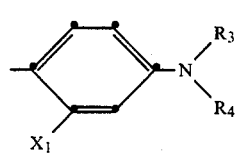

or a 3-indolyl radical of the formula

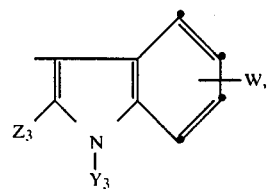

wherein

W is halogen or preferably hydrogen, $Y_3$ is hydrogen, $C_1$–$C_8$alkyl, acetyl, propionyl, benzyl or benzyl which is substituted by halogen, methyl or methoxy, $Z_3$ is lower alkyl or phenyl, $R_3$ and $R_4$ are each independently of the other lower alkyl, cyano-lower alkyl, cyclohexyl, benzyl, or benzyl which is substituted by halogen, methyl or methoxy, or $R_3$ and $R_4$, together with the nitrogen atom to which they are attached, are pyrrolidino, piperidino or morpholino, $X_1$ is hydrogen, halogen, lower alkyl, $C_1$–$C_8$alkoxy, benzloxy or the

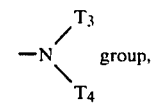

in which $T_3$ and $T_4$ are each independently of the other hydrogen, lower alkyl, formyl, lower alkylcarbonyl, benzoyl or benzoyl which is substituted by halogen, methyl or methoxy.

Halogen in connection with the above substituents in formulae (1) and (2) is for example fluorine, bromine or, preferably, chlorine.

Preferred azaphthalides of formula (2) are those wherein $Q_1$ is the radical of formula (2a), $X_1$ is lower alkyl, $C_1$–$C_8$alkoxy, in particular lower alkoxy, benzoyloxy, lower alkylcarbonylamino, benzoylamino or di-lower alkylamino, $Y_3$ is preferably $C_1$–$C_8$alkyl and the pyridine ring A is preferably mono- or disubstituted by $C_1$–$C_3$alkyl.

Particularly interesting ring-substituted 4-azaphthalides are those of formula

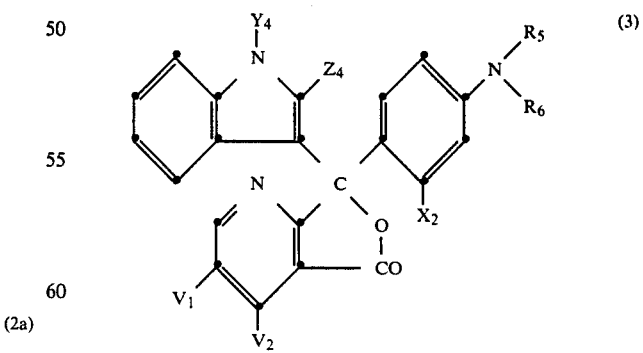

wherein one of $V_1$ and $V_2$ is $C_1$–$C_3$alkyl and the other is hydrogen or $C_1$–$C_3$alkyl, $Y_4$ is hydrogen, $C_1$–$C_8$alkyl or benzyl, $Z_4$ is phenyl or preferably methyl, $R_5$ and $R_6$ are each independently of the other lower alkyl, cyclohexyl or benzyl, or $-NR_5R_6$ is pyrrolidino, piperidino or morpholino, $X_2$ is methyl, lower alkoxy, benzyloxy, acetylamino, propionylamino, benzoylamino or di-lower alkylamino.

Among these compounds of formula (3), those compounds are particularly preferred in which $V_1$ is methyl, ethyl or, preferably, propyl, $V_2$ is hydrogen, $R_5$ is methyl, ethyl or cyclohexyl, $R_6$ is methyl or ethyl, or $-NR_5R_6$ is pyrrolidinyl, $X_5$ is lower alkoxy, preferably ethoxy, $Z_4$ is methyl, and $Y_4$ is methyl, ethyl, n-butyl, hexyl or, preferably, n-octyl.

The azaphthalides of formulae (1) to (3) are novel chromogenic compounds and can be prepared by methods which are known per se. One process for the preparation of the azaphthalides of formula (1) comprises reacting a compound of formula

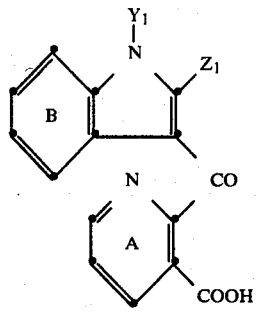 (4)

with a compound of formula

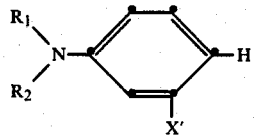 (5)

or of formula

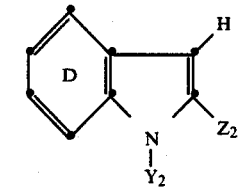 (6)

in which formulae above A, B, D, $Y_1$, $Y_2$, $Z_1$, $Z_2$, $R_1$ and $R_2$ have the given meanings and X' has the meaning of X or is hydroxy.

If X' is hydroxy or $-NT_1T_2$, wherein at least one of $T_1$ and $T_2$ is hydrogen, then the reaction product can be subsequently alkylated, aralkylated and/or acylated as defined herein.

Alternatively, the azaphthalides can be prepared by reacting a cmpound of formula

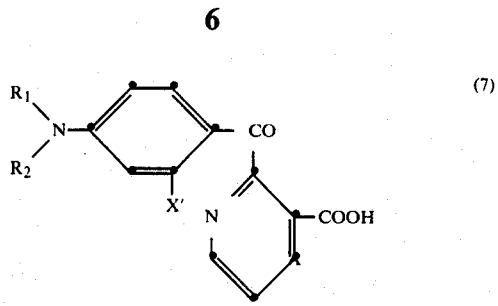 (7)

or of formula

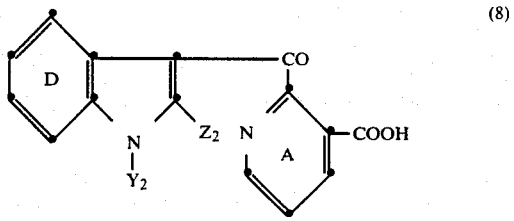 (8)

with an indole of formula

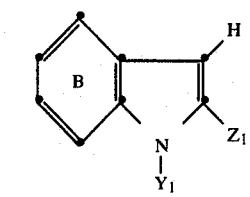 (9)

in which formulae A, B, D, $R_1$, $R_2$, $Y_1$, $Y_2$, $Z_1$ and $Z_2$ have the given meanings and X' has the meaning of X or is hydroxy, and the reaction product can be subsequently alkylated, aralkylated and/or acylated if X' is hydroxy or at least one of $T_1$ and $T_2$ is hydrogen.

The reactions are preferably carried out such that the reactants are reacted in the presence of an acid condensing agent in the temperature range from 20° to 140° C. Examples of such condensing agents are acetic anhydride, sulfuric acid, phosphoric acid and phosphoroxy chloride. The isolation of the final product of formula (1) is effected in known manner by adjusting the pH of the reation mixture to not less than 6, preferably to a value from 7 to 11, e.g. with an alkali such as an alkali metal hydroxide, ammonia, an alkali metal carbonate or bicarbonate, isolating the precipitate and washing and drying it, or by treatment with a suitable organic solvent such as methanol, isopropanol, benzene, chlorobenzene or, preferably, toluene. If mixtures of isomers are obtained, the individual 4- and 7-azaphthalides are separated by chromatography and/or recrystallisation.

The alkylation, aralkylation and/or acylation of the reaction product, in which X' is hydroxy or at least one of $T_1$ and $T_2$ is hydrogen, is usually carried out by known methods. For example, the reaction is carried out in the presence of an acid acceptor, e.g. an alkali metal carbonate or of a tertiary nitrogen base such as triethylamine, and in the absence or presence of an inert organic solvent such as acetone, isopropyl alcohol, chlorobenzene or nitrobenzene. Examples of suitable acylating agents are reactive functional derivatives of aliphatic carboxylic acids, in particular fatty acid halides and anhydrides, e.g. acetyl bromide, acetyl chloride or acetic anhydride, or of aromatic carboxylic acids such as benzoyl halides. Examples of suitable alkylating agents are alkyl halides such as methyl or ethyl iodide or methyl or ethyl chloride, or dialkyl sulfates such as dimethyl or diethyl sulfate. Suitable aralkylating agents are in particular benzyl chloride or the corresponding substitution products such as p-chlorobenzyl chloride or 2,4-dimethylbenzyl chloride, which are preferably used in a non-polar organic solvent such as benzene, toluene or xylene.

The compounds of formula (4), wherein $Y_1$ is acyl or an unsubstituted or substituted alkyl or benzyl group can likewise be prepared by conventional acylation, alkylation or aralkylation of the intermediate obtained by reacting the anhydride of formula (8) with an indole of formula (9), wherein $Y_1$ is hydrogen. The acylating, alkylating and aralkylating agents may be the same as those indicated for the preparation of the compounds of formulae (1) to (3).

The starting materials of formulae (4), (7) and (8) are usually obtained by reacting the anhydride of formula

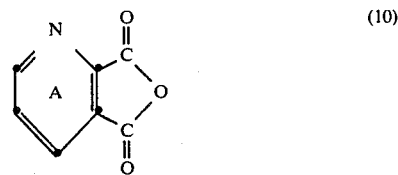

(10)

obtained from 2,3-pyridinedicarboxylic acid, with a compound of formula (9) or with a compound of formula (5) or (6), which reaction is carried out, if desired, in an organic solvent and preferably in the presence of an organic or inorganic metal salt, e.g. zinc chloride or aluminium chloride. Examples of suitable organic solvents are dimethylformamide, acetonitrile, propionitrile, lower aliphatic carboxylic acids, e.g. acetic acid or propionic acid, benzene, toluene, xylene or chlorobenzene. The reaction is preferably carried out in the temperature range from 5° C. to the boiling point of the solvent employed. The resultant compounds of formulae (4), (7) and (8) are further used, preferably without being isolated, for reaction with the anilines of formula (5) or with the indoles of formula (9).

The conversion of the substituted 2,3-pyridinedicarboxylic acid (quinolinic acid) into the anhydride is effected advantageously by heating the acid in acetic anhydride, evaporating the mixture to dryness and dissolving or suspending the dry residue in a lower carboxylic acid, e.g. acetic acid, and subsequently further using the resultant solution or suspension direct.

The substituted 2,3-pyridinedicarboxylic acid is prepared by treating a pyridinedicarboximide of formula

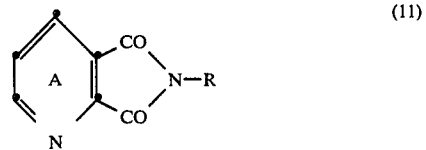

(11)

wherein A has the given meaning and R is lower alkyl or preferably phenyl, with a mineral acid, e.g. HCl, HBr, HI, $HClO_4$ or $H_2SO_4$, with elimination of the amine. Such substituted 2,3-pyridinedicarboxylic acids are described in European patent specification 161 221.

The preparation of the azaphthalides of formula (1) is preferably carried out in two steps utilising a single vessel and without isolating the intermediate.

The first step, in which the quinolinyl anhydride of formula (10) is reacted with an indole of formula (9) in an organic solvent consisting of a lower aliphatic carboxylic acid or a nitrile thereof, and in the presence of an organic or inorganic metal salt, is preferably carried out in the temperature range from 0° to 60° C., most preferably at room temperature (17°–30° C.).

The lower aliphatic carboxylic acid employed as reaction medium is conveniently a carboxylic acid which is liquid under the reaction conditions and contains 1 to 5 carbon atoms. Suitable aliphatic carboxylic acids which form the reaction medium are formic acid, acetic acid, dichloroacetic acid, propionic acid, butyric acid, isobutyric acid, valeric acid, or mixtures of such acids.

Suitable nitriles which can also be used as reaction medium are e.g. acetonitrile, propionitrile or butyronitrile.

The metal salts employed are advantageously derived from polyvalent metals having an atomic weight in the range from 24 to 210, preferably from 26 to 140 and, most preferably, from 26 to 120. Examples of such metals are aluminium, barium, lead, cadmium calcium, chromium, iron, gallium, cobalt, copper, magnesium, manganese, molybdenum, nickel, mercury, strontium, tantalum, titanium, vanadium, tungsten, zinc, tin and zirconium, Preferred metals are aluminium, calcium, cadmium, iron, chromium, cobalt, copper, nickel, manganese, strontium, tin and zinc. The anionic component of these metal salts is preferably derived from a mineral acid or also from an inorganic salt and is e.g. a sulfate, halide, nitrate, formate, acetate, propionate, citrate or stearate. The metal salts may be employed singly or as mixtures.

The amount of metal salt in the first reaction step is conveniently 10 to 100 mol %, preferably 12 to 50 mol %, based on the quinolinyl anhydride employed.

Upon completion of the first reaction step, the reaction product (non-isolated ketonic acid) is further condensed direct with the compound of formula (5) or (6). This second reaction step is preferably carried out such that the reaction components are reacted in the presence of the acid condensing agent in the temperature range from 20° to 80° C.

The azaphthalides of formulae (1) to (3) are normally colourless or, at most, faintly coloured. When these colour formers are brought into contact with preferably an acid developer, e.g. an electron acceptor, they produce, depending on the meaning of Q and X and on the developer employed, strong red, violet, greenish-blue, blue or violet-blue shades of excellent fastness to sublimation and light.

They are therefore also very useful when combined with one or more other known colour formers, for example, 3,3-(bisaminophenyl)phthalides, 3,3-(bisindolyl)phthalides, 3-aminofluoranes, 2,6-diaminofluoranes, 2,6-diamino-3-methylfluoranes, leucoauramines, spiropyranes, spirodipyranes, chromenoindoles, chromenopyrazoles, phenoxazines, phenothiazines, quinazolines, rhodamine lactams, carbazolylmethanes or other triarylmethananeleuco dyes, to give blue, navy blue, grey or black colorations.

The azaphthalides of the formulae (1) to (3) exhibit on activated clays as well as especially on phenolic substrates an improved colour intensity and lightfastness.

They are suitable in particular as rapidly developing colour formers for use in a heat-sensitive, or especially in a pressure-sensitive, recording material which can also be a copying material. They are distinguished by the property that they are pH-stable and that they are highly soluble in the capsule oils. After exposure on a CB sheet, they exhibit a slight decrease in colour strenght (CB decline).

A pressure-sensitive material consists, for example, of at least one pair of sheets which contain at least one colour former of the formulae (1) to (3), dissolved in an organic solvent, and an electron acceptor as developer.

Typical examples of such developers are activated clays such as attapulgite, acid clay, bentonite, montmorillonite, activated clay, e.g. acid-activated bentonite or montmorillonite, and also zeolith, halloysite, silica, alumina, aluminium sulfate, aluminium phosphate, zinc chloride, zinc nitrate, activated kaolin or any clay. Suitable developers are also acidic organic compounds, for example unsubstituted or ring-substituted phenol, resorcinols, salicyclic acids e.g. 3,5-bis($\alpha$-methylbenzyl)salicylic acid or 3,5-bis(2-methylbenzyl)saliciylic acid, or salicylates and their metal salts, e.g. zinc salts, or an acidic polymer, for example a phenolic polymer, an alkylphenol acetylene resin, a maleic acid/rosin resin or a partially or completely hydrolysed polymer of maleic acid and styrene, ethylene or vinyl methyl ether, or carboxypolymethylene. Mixtures of these monomers and polymers can also be used. Particularly preferred developers are acid-activated bentonite, zinc salicylates or the condensates of p-substituted phenols with formaldehyde. These latter may also be modified with zinc.

The developers may also be used in admixture with other basically inert or almost inert pigments or with other auxiliaries such as silica gel or UV absorbers, e.g. 2-(2-hydroxyphenyl)benzotriazoles. Examples of such pigments are: talcum, titanium dioxide, zinc oxide, chalk, clays such as kaolin, as well as organic pigments, e.g. urea/formaldehyde condensates (BET surface area: 2–75 $m^2/g$) or melamine/formaldehyde condensates.

The colour former effects a coloured marking at those points where it comes into contact with the electron acceptor. To prevent the colour formers contained in the pressure-sensitive recording material from becoming active prematurely, they are usually separated from the electron acceptor. This separation can conveniently be accomplished by incorporating the colour formers in foam-like, sponge-like or honeycomb-like structures. The colour formers are preferably encapsulated in microcapsules, which as a rule can be ruptured by pressure.

When the capsules are ruptured by pressure, for example with a pencil, the colour former solution is transferred to an adjacent sheet which is coated with an electron acceptor and a coloured area is thus produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example a polyhalogenated paraffin, such as chloroparaffin, or a polyhalogenated diphenyl, such as monochlorodiphenyl or trichlorodiphenyl, and also tricresyl phosphate, di-n-butyl phthalate, dioctyl phthalate, trichlorobenzene, trichloroethyl phosphate, an aromatic ether such as benzylphenyl ether, a hydrocarbon oil such as paraffin or kerosene, an alkylated, e.g. an isopropyl, isobutyl, sec- or tert-butyl, derivative of diphenyl, diphenylalkane, naphthalene or terphenyl; dibenzyl toluene, terphenyl, partially hydrogenated terphenyl, a benzylated xylene, or other chlorinated or hydrogenated, condensed aromatic hydrocarbons. Mixtures of different solvents, especially mixtures of paraffin oils or kerosene and diisopropylnaphthalene or partially hydrogenated terphenyl, are often used in order to obtain an optimum solubility for the colour formation, a rapid and intense coloration, and a viscosity which is advantageous for the microencapsulation. When encapsulated, the ring-substituted azaphthalides are distinguished by exceedingly good pH stability, e.g. in the pH range from 4 to 10.

The capsules walls can be formed evenly around the droplets of the colour former solution by coacervation; and the encapsulating material can consist of gelatin and gum arabic, as described e.g. in U.S. Pat. No. 2 800 457. The capsules can also be formed preferably from an aminoplast or a modified aminoplast by polycondensation, as described in British patent specification Nos. 982 264, 1 156 725, 1 301 052 and 1 355 124. Also suitable are microcapsules which are formed by interfacial polymerisation, e.g. capsules formed from polyester, polycarbonate, polysulfonamide, polysulfonate, but in particular from polyamide or polyurethane.

The microcapsules containing the colour formers of the formulae (1) to (3) can be used for the production of a wide range of known kinds of pressure-sensitive copying materials. The various systems differ substantially from one another in the arrangement of the capsules, of the colour reactants, and of the support. A preferred arrangement is that in which the encapsulated colour former is in the form of a layer on the back of a transfer sheet and the developer is in the form of a layer on the face of a receiver sheet.

Another arrangement of the components is that wherein the microcapsules containing the colour former and the developer are in or on the same sheet, in the form of one or more individual layers, or are present in the paper pulp.

The capsules are preferably secured to the support by means of a suitable adhesive. As paper is the preferred support, these adhesives are principally paper-coating agents, for example gum arabic, polyvinyl alcohol, hydroxymethylcellulose, casein, methyl cellulose, dextrin, starch or starch derivatives or polymer latices. These latter are e.g. butadiene/styrene copolymers or acrylic homopolymers or copolymers.

The paper employed comprises not only normal paper made from cellulose fibres, but also paper in which the cellulose fibres are replaced (partially or completely) by synthetic polymers.

The compounds of formulae (1) to (3) can also be employed as colour formers in a thermoreactive recording material. This recording material usually contains at least one carrier, one colour former, one electron acceptor and, optionally, also a binder and/or wax.

Thermoreactive recording systems comprises, for example, heat-sensitive recording or copying materials or papers. These systems are used e.g. for recording information, for example in electronic computers, teleprinters or telewriters, or in recording and measuring instruments, e.g. electrocardiographs. The image (mark) information can also be affected manually with a heated pen. Laser beams can also be used to produce heat-induced marks.

The thermoreactive recording material can be composed such that the colour former is dispersed or dissolved in one binder layer and the developer is dissolved or dispersed in the binder in a second layer.

Another possibility comprises in dispersing both the colour former and the developer in one layer. By means of heat the binder is softened at specific areas and the colour former comes into contact with the electron acceptor at those points where heat is applied and the desired colour develops at once.

Suitable developers are the same electron acceptors as are used in pressure-sensitive papers. Examples of developers are the already mentioned clays and phenolic resins, or also the phenolic compounds described e.g. in German Offenlegungsschrift No. 1 251 348, for example 4-tert-butylphenol, 4-phenylphenol, methylene-bis(p-phenylphenyol), 4-hydroxydiphenyl ether, α-naphthol, β-naphthol, methyl 4-hydroxybenzoate or benzyl 4-hydroxybenzoate, 4-hydroxydiphenylsulfone, 4'-hydroxy-4-methyldiphenylsulfone, 4-hydroxyacetophenone, 2,2'-dihydroxydiphenyl, 4,4'-isopropylidenediphenol, 4,4'-isopropylidenebis(2-methylphenol), 4,4'-bis(hydroxyphenyl) valeric acid, hydroquinone, pyrogallol, phloroglucinol, p-, m- and o-hydroxybenozic acid, gallic acid, 1-hydroxy-2-naphthoic acid, as well as boric acid or organic, preferably aliphatic, dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the azaphthalides and the developer are sparingly soluble or insoluble in water. The binder should be able to disperse and fix the colour former and the developer at room temperature.

By applying heat the binder softens or melts, so that the colour former comes in contact with the developer and a colour is able to form. Examples of binders which are soluble, or at least swellable, in water are e.g. hydrophilic polymers such as polyvinyl alcohol, polyacrylic acid, hydroxyethylcellulose, methyl cellulose, carboxymethylcellulose, polyacrylamide, polyvinyl pyrrolidone, gelatin, starch, or etherified corn starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyd resins, polystyrene, styrene/butadiene copolymers, polymethylacrylates, ethyl cellulose, nitricellulose or polyvinyl carbazole. The preferred arrangement, however, is that in which the colour former and the developer are contained in one layer in a water-soluble binder.

The thermoreactive coatings may contain further ingredients. To improve the degree of whiteness, to facilitate the printing of papers, and to prevent the heated pen from sticking, the coatings may contain e.g. talcum, titanium dioxide, zinc oxide, aluminium hydroxide, calcium carbonate (e.g. chalk), clays or also organic pigments, for example urea/formaldehyde polymers. In order to effect the colour formation only within a limited temperature range, it is possible to add substances such as urea, thiourea, diphenyl thiourea, acetamide, acetanilide, stearylamide, phthalic anhydride, metal stearates such as zinc stearate, dimethyl terephthalate, phthalonitrile or other appropriate fusible products which induce the simultaneous melting of the colour former and the developer. Thermographic recording materials preferably contain waxes, e.g. carnauba wax, montan wax, paraffin wax, polyethylene wax, condensates of higher fatty acid amides and formaldehyde, or condensates of higher fatty acids and ethylenediamine.

The invention is illustrated by the following Examples, in which percentages are by weight, unless otherwise indicated.

EXAMPLE 1

1.9 g of 5-propyl-2,3-pyridinedicarboxylic anhydride (m.p. 42°-44° C.), 0.4 g of zinc chloride, 15 ml of glacial acetic acid and 2.9 g of N-octyl-2-methylindole are stirred for 5 hours at room temperature. Then 5 ml of acetic anhydride and 2 g of 3-(N,N-diethylamino)-phenetol are added, after which the reaction mixture is heated to 55°-60° C. and stirred for 2 hours at this temperature. The reaction mixture is adjusted to pH 6-7 with aqueous sodium hydroxide solution and extracted with toluene, whereupon two phases form and are then separated. The organic phase is washed with water, dried over sodium sulfate and chromatographed through a column of silica gel which is eluted with a 4:1 mixture of toluene/ethyl acetate.

Yield: 5 g of the 4-azaphthalide of formula

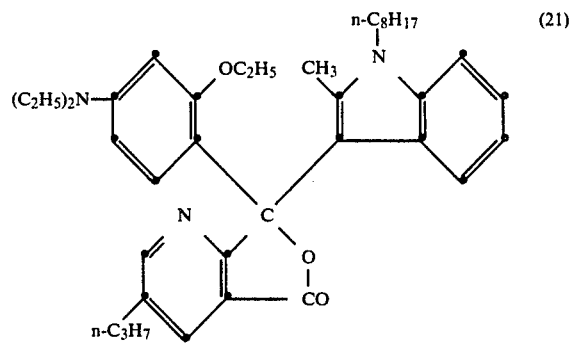

with a melting point of 116°-118° C. This colour former develops a strong blue colour on phenolic resin.

The 5-propyl-2,3-pyridinedicarboxylic acid employed in this Example is prepared as follows:

2.67 g of 5-propylpyridine-N-phenyl-2,3-dicarboximide (m.p. 149°-151° C.) and 50 ml of concentrated hydrochloric acid are boiled under reflux for 4 hours. Then the reaction mixture is concentrated by evaporation and 100 ml of ice-water are added to the residue. The crystallised product is isolated by filtration, washed with water and dried in vacuo at 70° C., affording 1.5 g of the dicarboxylic acid of formula

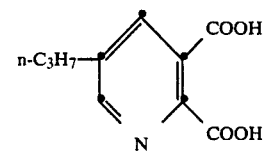

with a melting point of 163°-165° C. (decomposition).

1.5 g of 5-propyl-2,3-dicarboxylic acid and 10 ml of acetic anhydride are stirred for 2 hours at 110° C. The mixture is then evaporated to dryness and the residue is dried in vacuo at 80° C., affording 1.35 g of 5-propyl-2,3-dicarboxylic anhydride.

EXAMPLE 2

1.9 g of 5-propyl-2,3-pyridinedicarboxylic anhydride, 0.4 g of zinc chloride, 15 ml of glacial acetic acid and 1.8 g of N-ethyl-2-methylindole are stirred for 5 hours at room temperature. Then 5 ml of acetic anhydride and 2 g of 3-(N,N-diethylamino)phenetol are added, after which the reaction mixture is heated to 55°-60° C. and stirred for 2 hours at this temperature. The reaction mixture is adjusted to pH 6–7 with aqueous sodium hydroxide solution and extracted with toluene, whereupon two phases form and are then separated. The organic phase is washed with water, dried over sodium sulfate and chromatographed through a column of silica gel which is eluted with a 4:1 mixture of toluene/ethyl acetate. Yield: 3.2 g of the 4-azaphthalide of formula

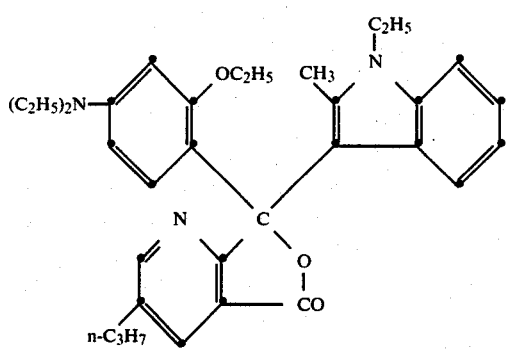
(22)

with a melting point of 171°–172° C. This colour former develops a strong blue colour on phenolic resin.

Using the appropriate starting materials, the ring-substituted azaphthalides of the formula

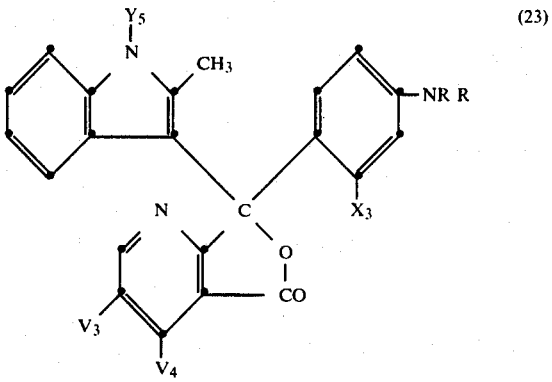
(23)

listed in Table 1 are obtained in the same manner as described in Examples 1 and 2.

TABLE 1

| Ex. | $V_3$ | $V_4$ | $Y_5$ | $X_3$ | —NR R | m.p./°C. |
|---|---|---|---|---|---|---|
| 3 | n-$C_3H_7$ | H | —$C_2H_5$ | H | —N($CH_3$)$_2$ | 130–132 |
| 4 | n-$C_3H_7$ | H | —$C_2H_5$ | $CH_3$ | —N($CH_3$)$_2$ | 175–177 |
| 5 | n-$C_3H_7$ | H | —$C_2H_5$ | —$OC_2H_5$ | —N(CH$_3$)-C$_6$H$_4$-H | 197–199 |
| 6 | n-$C_3H_7$ | H | —$C_2H_5$ | —$OC_2H_5$ | —NH-C$_6$H$_4$ | 169–171 |
| 7 | n-$C_3H_7$ | H | —$C_2H_5$ | —OCH$_2$-C$_6$H$_5$ | —N($C_2H_5$)$_2$ | 105–107 |
| 8 | n-$C_3H_7$ | H | —$C_2H_5$ | —NHCOCH$_3$ | —N($C_2H_5$)$_2$ | 110–112 |
| 9 | n-$C_3H_7$ | H | —$C_8H_{17}$ | —NHCOCH$_3$ | —N($C_2H_5$)$_2$ | 129–132 |
| 10 | n-$C_3H_7$ | H | —$C_8H_{17}$ | H | —N($CH_3$)$_2$ | oil |
| 11 | n-$C_3H_7$ | H | —$C_8H_{17}$ | $CH_3$ | —N($CH_3$)$_2$ | oil |
| 12 | n-$C_3H_7$ | H | —$C_8H_{17}$ | —$OC_2H_5$ | —N(CH$_3$)-C$_6$H$_4$-H | oil |
| 13 | n-$C_3H_7$ | H | —$C_8H_{17}$ | —$OC_2H_5$ | —NH-C$_6$H$_4$ | oil |

TABLE 1-continued

| Ex. | V₃ | V₄ | Y₅ | X₃ | —NR R | m.p./°C |
|---|---|---|---|---|---|---|
| 14 | n-C₃H₇ | H | —C₈H₁₇ | —OCH₂—(phenyl) | —N(C₂H₅)₂ | oil |
| 15 | —C₂H₅ | (fused benzo) | —C₈H₁₇ | —OC₂H₅ | —N(C₂H₅)₂ | oil |
| 16 | —CH₃ | —C₂H₅ | —C₂H₅ | —OC₂H₅ | —N(C₂H₅)₂ | 164–166 |
| 17 | —CH₃ | —C₂H₅ | —C₈H₁₇ | —OC₂H₅ | —N(C₂H₅)₂ | 86–89 |
| 18 | —C₂H₅ | (fused benzo) | —C₂H₅ | —OC₂H₅ | —N(C₂H₅)₂ | 201–203 |
| 19 | —CH₂—CH₂—CH₂—CH₂— | | —C₈H₁₇ | —OC₂H₅ | —N(C₂H₅)₂ | oil |

EXAMPLE 20

1.92 g of 5-propyl-2,3-pyridinedicarboxylic anhydride 0.4 g of zinc chloride, 15 ml of glacial acetic acid and 3.2 g of N-ethyl-2-methylindole are stirred for 5 hours at room temperature. Then 5 ml of acetic anhydride are added and the reaction mixture is stirred for another 2 hours at this temperature. The reaction mixture is adjusted to pH 10–11 with aqueous sodium hydroxide solution and extracted with toluene, whereupon two phases form and are then separated. The toluene phase is washed with water, dried over sodium sulfate and chromatographed through a column of silica gel which is eluted with a 4:1 mixture of toluene/ethyl acetate.

Yield: 3.8 g of a 3,3-bisindolyl-4-azaphthalide of formula

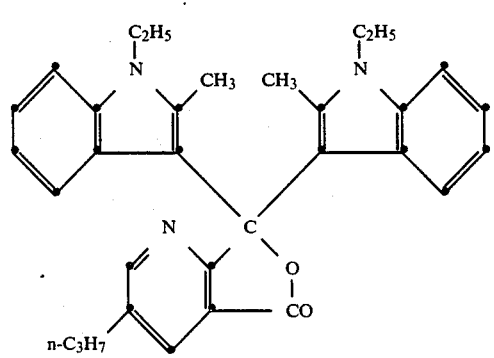
(24)

with a melting point of 193°–194° C. This colour former develops a strong reddish violet colour on phenolic resin.

Using the appropriate starting materials, the 3,3-bisindolyl-4-azaphthalides of the formula

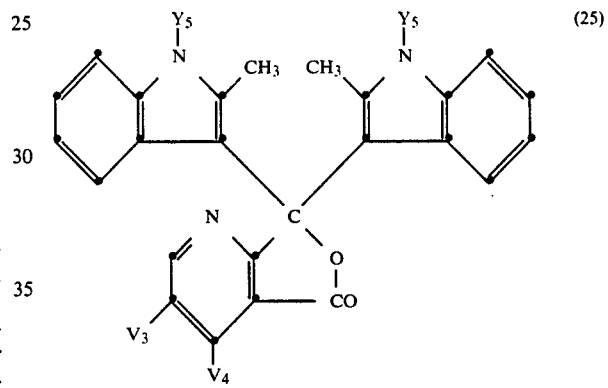
(25)

listed in Table 2 are prepared in the same manner as described in Example 20.

TABLE 2

| Ex. | V₃ | V₄ | Y₅ | m.p./°C |
|---|---|---|---|---|
| 21 | n-C₃H₇ | H | —n-C₈H₁₇ | 81–83 |
| 22 | —CH₃ | —C₂H₅ | —C₂H₅ | 133–138 |
| 23 | —C₂H₅ | —n-C₃H₇ | —C₂H₅ | 156–158 |
| 24 | —C₂H₅ | (fused benzo) | —C₂H₅ | 198–200 |
| 25 | —C₂H₅ | (fused benzo) | —n-C₈H₁₇ | 90–91 |
| 26 | —CH₂—CH₂—CH₂—CH₂— | | —n-C₈H₁₇ | 106–108 |

EXAMPLE 27

Preparation of a pressure-sensitive copying paper

A solution of 3 g of the azaphthalide of the formula (21) obtained in Example 1 in 80 g of diisopropylnaphthalene and 17 g of kerosene are microencapsulated by coacervation in a manner known per se with gelatin and gum arabic. The microcapsules are mixed with starch solution and coated on a sheet of paper. The face of a second sheet of paper is coated with phenolic resin as colour developer. The first sheet and the sheet coated with the developer are laid on top of each other with the coated sides face to face. Pressure is exerted on the first sheet by writing by hand or typewriter and a strong blue copy of excellent fastness to sublimation and light develops immediately on the sheet coated with the developer. Strong blue and reddish-violet copies which are fast to sublimation and light are also obtained by using any of the other colour formers indicated in Examples 2 to 26.

EXAMPLE 28

1 g of the azaphthalide obtained in Example 2 is dissolved in 17 g of toluene. With stirring, 12 g of polyvinyl acetate, 8 g of calcium carbonate and 2 g of titanium dioxide are added to this solution. The resultant suspension is diluted with toluene in the weight ratio 1:1 and applied to a sheet of paper with a knife to a thickness of 10 μm. On this sheet of paper is laid a second sheet, the underside of which has been coated to a weight of 3 g/m² with a mixture consisting of 1 part of an amide wax, 1 part of a stearin wax and 1 part of zinc chloride. Pressure is exerted on the top sheet by hand or typewriter and a strong and lightfast blue copy develops immediately on the sheet coated with the colour former.

EXAMPLE 29

Preparation of a heat-sensitive recording material

In a ball mill, 32 g of 4,4'-isopropylidenediphenol (bisphenol A), 3.8 g of the distearylamide of ethylenediamine, 39 g of kaolin, 20 g of an 88% hydrolysed polyvinylalcohol and 500 ml of water are ground to a particle size of about 5 μm. In a second ball mill, 6 g of the azaphthalide obtained in Example 1, 3 g of a 88% hydrolysed polyvinyl alcohol and 60 ml of water are ground to a particle size of about 3 μm. Both dispersions are mixed and applied to paper to a dry coating weight of 5.5 g/m². A strong blue colour of excellent fastness to light and sublimation is produced by contacting the paper with a heated ball-point pen. Strong and lightfast blue and reddish-violet copies can also be obtained by using any of the other colour formers obtained in Examples 2 to 26.

What is claimed is:

1. A ring-substituted 4-azaphthalide of formula

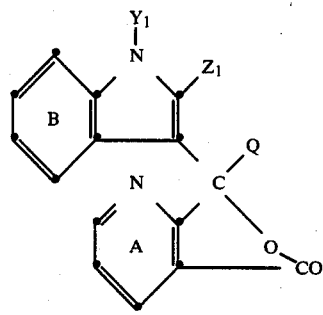

wherein

Q is a substituted phenyl radical of the formula

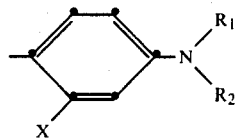

or a 3-indolyl radical of the formula

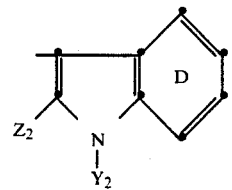

$Y_1$ and $Y_2$ are each independently of the other hydrogen, alkyl of not more than 12 carbon atoms which is unsubstituted or substituted by halogen, hydroxyl, cyano or lower alkoxy, or are $C_1$-$C_{12}$acyl, benzyl, or benzyl which is substituted by halogen, cyano, lower alkyl or lower alkoxy, $Z_1$ and $Z_2$ are each independently of the other hydrogen, lower alkyl or phenyl, $R_1$ and $R_2$ are each independently of the other hydrogen, alkyl of not more than 12 carbon atoms which is unsubstituted or substituted by halogen, hydroxy, cyano or lower alkoxy, or are $C_5$-$C_{10}$cycloalkyl, or benzyl or phenyl, each unsubstituted or substituted by halogen, cyano, lower alkyl or lower alkoxy; or $R_1$ and $R_2$, together with the nitrogen atom to which they are attached, are a 5- or 6-membered saturated heterocyclic ring, X is hydrogen, halogen, lower alkyl, $C_1$-$C_{12}$alkoxy, $C_1$-$C_{12}$acyloxy, benzyl, phenyl, benzyloxy, phenoxy, benzyl or benzyloxy which are each substituted by halogen, cyano, lower alkyl or lower alkoxy, or is the $-NT_1T_2$ group, in which $T_1$ and $T_2$, each independently of the other, are hydrogen, lower alkyl, cycloalkyl, benzyl, or benzyl which is substituted by halogen, cyano, lower alkyl or lower alkoxy, or is $C_1$-$C_{12}$acyl, and $T_1$ is also phenyl, or phenyl which is substituted by halogen, cyano, lower alkyl or lower alkoxy, and wherein the pyridine ring A is substituted by lower alkyl, lower alkoxy, lower alkylthio, phenyl, phenoxy, or phenyl or phenoxy which are each substituted by halogen, cyano, lower alkyl, lower alkoxy or cyano-lower alkyl, or by tetramethylene, and the benzene nuclei B and D, each independently of the other, are unsubstituted or substituted by halogen, cyano, lower alkyl, lower alkoxy, lower alkoxycarbonyl, amino, mono-lower alkylamino or di-lower alkylamino.

2. An azaphthalide according to claim 1, wherein the pyridine ring A in formula (1) is substituted by $C_1$-$C_4$alkyl.

3. An azaphthalide according to claim 1, wherein the rings B and D in formula (1) are not further substituted.

4. An azaphthalide according to claim 1, wherein $Y_1$ and $Y_2$ in formula (1) are $C_1$-$C_8$alkyl, benzyl, acetyl or propionyl.

5. An azaphthalide according to claim 1, wherein $R_1$ and $R_2$ in formula (1) are each independently of the other lower alkyl, cyclohexyl, benzyl or cyano-lower alkyl, or —NR$_1$R$_2$ is pyrrolidinyl.

6. An azaphthalide according to claim 1, wherein X in formula (1) is hydrogen, halogen, benzyloxy, lower alkyl, C$_1$-C$_8$alkoxy or —NT$_1$T$_2$, wherein one of T$_1$ and T$_2$ is lower alkyl or C$_1$-C$_8$acyl and the other is hydrogen or lower alkyl.

7. An azaphthalide according to claim 1 of the formula

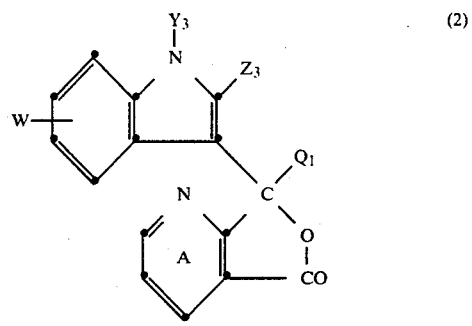
(2)

wherein
Q$_1$ is a substituted phenyl radical of the formula

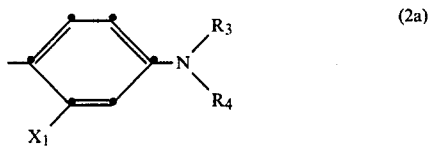
(2a)

or a 3-indolyl radical of the formula

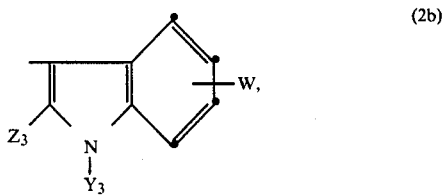
(2b)

wherein
W is hydrogen or halogen,
Y$_3$ is hydrogen, C$_1$-C$_8$alkyl, acetyl, propionyl, benzyl or benzyl which is substituted by halogen, methyl or methoxy,
Z$_3$ is loer alkyl or phenyl,
R$_3$ and R$_4$ are each independently of the other lower alkyl, cyano-lower alkyl, cyclohexyl, benzyl, or benzyl which is substituted by halogen, methyl or methoxy; or R$_3$ and R$_4$, together with the nitrogen atom to which they are attached, are pyrrolidino, piperidino or morpholino;
X$_1$ is hydrogen, halogen, lower alkyl, C$_1$-C$_8$alkoxy, benzyloxy or the

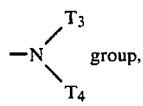 group, in which
T$_3$ and T$_4$ are each independently of the other hydrogen, lower alkyl, formyl, lower alkylcarbonyl, benzoyl, or benzoyl which is substituted by halogen, methyl or methoxy.

8. An azaphthalide according to claim 7, wherein Q$_1$ in formula (2) is the radical of formula (2a).

9. An azaphthalide according to claim 7, wherein X$_1$ in formula (2) is lower alkyl, C$_1$-C$_8$alkoxy, benzyloxy, lower alkylcarbonylamino, benzoylamino or di-lower alkylamino.

10. An azaphthalide according to claim 7, wherein Y$_3$ in formula (2) is C$_1$-C$_8$alkyl.

11. An azaphthalide according to claim 7, wherein the pyridine ring A in formula (2) is mono- or disubstituted by C$_1$-C$_3$alkyl.

12. A ring-substituted 4-azaphthalide of the formula

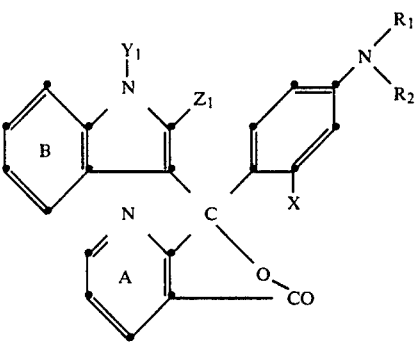

wherein
Y$_1$ is hydrogen, C$_1$-C$_{12}$alkyl which is unsubstituted or substituted by halogen, hydroxyl, cyano or lower alkoxy, or are C$_1$-C$_{12}$acyl, benzyl, or benzyl which is substituted by halogen, cyano, lower alkyl or lower alkoxy;
Z$_1$ is hydrogen, lower alkyl or phenyl;
R$_1$ and R$_2$ are each independently of the other hydrogen, C$_1$-C$_{12}$alkyl which is unsubstituted or substituted by halogen, hydroxy, cyano or lower alkoxy, or are C$_5$-C$_{10}$cycloalkyl, or benzyl or phenyl, each unsubstituted or substituted by halogen, cyano, lower alkyl or lower alkoxy; or R$_1$ and R$_2$, together with the nitrogen atom to which they are attached, are a 5- or 6-membered saturated heterocyclic ring; and
X is hydrogen, halogen, lower alkyl, C$_1$-C$_{12}$alkoxy, C$_1$-C$_{12}$acyloxy, benzyl, phenyl, benzyloxy, phenoxy, benzyl or benzyloxy which are each substituted by halogen, cyano, lower alkyl or lower alkoxy, or is the —NT$_1$T$_2$ group, in which T$_1$ and T$_2$, each independently of the other, are hydrogen, lower alkyl, cycloalkyl, benzyl, or benzyl which is substituted by halogen, cyano, lower alkyl or lower alkoxy, or is C$_1$-C$_{12}$acyl, and T$_1$ is also phenyl, or phenyl which is substituted by halogen, cyano, lower alkyl or lower alkoxy; and
wherein the pyridine ring A is substituted by lower alkyl, lower alkoxy, lower alkylthio, phenyl, phenoxy, or phenyl or phenoxy which are each substituted by halogen, cyano, lower alkyl, lower alkxy or cyano-lower alkyl, or by tetramethylene; and
the benzene nucleus B is unsubstituted or substituted by halogen, cyano, lower alkyl, lower alkoxy, lower alkoxycarbonyl, amino, mono-lower-alkylamino or di-lower-alkylamino.

13. An azaphthalide according to claim 12 wherein R$_1$ and R$_2$ are each independently of the other hydrogen; $C_1$-$C_{12}$alkyl which is unsubstituted or substituted by halogen, hydroxy, cyano or lower alkoxy; or benzyl or phenyl, each unsubstituted or substituted by halogen, cyano, lower alkyl or lower alkoxy; or $R_1$ and $R_2$, together with the nitrogen atom to which they are attached, are a 5- or 6-membered saturated heterocyclic ring.

14. An azaphthalide according to claim 12, of the formula $$\tag{3}$$

wherein
one of $V_1$ and $V_2$ is $C_1$-$C_3$alkyl and theother is hydrogen or $C_1$-$C_3$alkyl,
$Y_4$ is hydrogen, $C_1$-$C_8$alkyl or benzyl,
$Z_4$ is methyl or phenyl,
$R_5$ and $R_6$ are each independently of the other lower alkyl, cyclohexyl or benzyl, or —$NR_5R_6$ is pyrrolidono, piperidino or morpholino, and
$X_2$ is methyl, lower alkoxy, benzyloxy, acetylamino, propionylamino, benzoylamino or di-lower alkylamino.

15. An azaphthalide according to claim 14, wherein
$V_1$ is methyl, ethyl or propyl,
$V_2$ is hydrogen,
$R_5$ is methyl, ethyl or cyclohexyl,
$R_6$ is methyl or ethyl, or —$NR_5R_6$ is pyrrolidinyl,
$X_5$ is lower alkoxy,
$Z_4$ is methyl, and
$Y_4$ is methyl, ethyl, n-butyl, hexyl or n-octyl.

16. The azaphthalide of claim 15, wherein $V_1$ is propyl, $R_5$ and $R_6$ are ethyl, $X_5$ is ethoxy, $Z_4$ is methyl and $Y_4$ is ethyl or n-octyl.

* * * * *